United States Patent
Hunt et al.

(10) Patent No.: US 6,339,169 B1
(45) Date of Patent: Jan. 15, 2002

(54) METHOD OF QUENCHING GASEOUS ACRYLONITRILE AND HYDROGEN CYANIDE PRODUCT STREAM

(75) Inventors: Charles R. Hunt, Friendswood, TX (US); Daniel E. Steinmeyer, Chesterfield, MO (US)

(73) Assignee: Solutia Inc., St. Louis, MO (US)

(*) Notice: Subject to any disclaimer, the term of this patent is extended or adjusted under 35 U.S.C. 154(b) by 0 days.

(21) Appl. No.: 09/372,005

(22) Filed: Aug. 11, 1999

Related U.S. Application Data

(60) Provisional application No. 60/102,316, filed on Sep. 29, 1998.

(51) Int. Cl.[7] ............................................. C07C 253/26
(52) U.S. Cl. ........................................ 558/319; 558/320
(58) Field of Search ................................. 558/319, 320

(56) References Cited

U.S. PATENT DOCUMENTS

| | | | |
|---|---|---|---|
| 2,340,547 A | 2/1944 | Mikami | |
| 3,472,892 A | 10/1969 | Callahan et al. | 260/465.3 |
| 3,549,685 A | 12/1970 | Badham et al. | 260/465.8 |
| 3,652,642 A | 3/1972 | Baba | 260/465.8 |
| 3,803,805 A | 4/1974 | Low | 55/73 |
| 3,885,928 A | 5/1975 | Wu | 55/85 |
| 3,936,360 A | 2/1976 | Wu | 203/75 |
| 4,166,008 A | 8/1979 | Wu et al. | 203/85 |
| 4,334,965 A | 6/1982 | Wu | 203/25 |
| 4,341,535 A | 7/1982 | Wu et al. | 55/85 |
| 4,530,826 A | 7/1985 | Ohashi et al. | 423/376 |
| 4,554,054 A | 11/1985 | Coyle | 203/15 |
| 4,588,508 A | 5/1986 | Allenson et al. | 210/708 |
| 4,699,951 A | 10/1987 | Allenson et al. | 525/194 |
| 4,820,782 A | 4/1989 | Ueno | 525/454 |
| 5,179,215 A | 1/1993 | Ramachandran et al. | 549/262 |
| 5,288,473 A | 2/1994 | Shaw et al. | 423/237 |
| 5,410,077 A | 4/1995 | Wu et al. | 549/529 |
| 5,457,223 A | 10/1995 | Shaw et al. | 558/319 |
| 5,466,857 A | 11/1995 | Reiling et al. | 558/319 |
| 5,534,650 A | 7/1996 | Ushikubo et al. | 558/319 |
| 5,646,304 A | 7/1997 | Acharya et al. | 549/259 |

FOREIGN PATENT DOCUMENTS

| | | |
|---|---|---|
| EP | 0 009545 | 12/1982 |
| WO | WO 93/10082 | 5/1993 |

*Primary Examiner*—Floyd D. Higel
*Assistant Examiner*—Ebenezer Sackey
(74) *Attorney, Agent, or Firm*—Howrey Simon Arnold & White LLP

(57) ABSTRACT

The present invention provides an improvement in a process and apparatus for manufacturing acrylonitrile by the vapor phase ammoxidation of a hydrocarbon. The invention comprises contacting the gaseous product stream with a quench fluid in a reverse jet scrubber. The quenching fluid is injected counter-current to the gas flow, and the gas velocity is sufficient to reverse the flow direction of the water, thereby forming a standing wave or froth zone wherein the quench is rapidly achieved. The quench fluid may be obtained from many sources, but is preferably obtained from a waste process stream emanating from a subsequent recovery or purification step. The quench fluid may contain acid to facilitate removal of ammonia from the gas stream. The quench fluid that is not vaporized may be recirculated. Impurities and contaminants may be removed from the quench fluid prior to recycle. In a most preferred embodiment, the quench fluid is not cooled during recirculation, and the cooling process is essentially adiabatic, with the sensible heat of the hot gaseous stream being converted to latent heat in the form of vapor.

27 Claims, 1 Drawing Sheet

US 6,339,169 B1

METHOD OF QUENCHING GASEOUS ACRYLONITRILE AND HYDROGEN CYANIDE PRODUCT STREAM

This application claims benefit to provisional application No. 60/102,316 filed Sep. 29, 1998.

The present invention is directed to a process for producing a petrochemical from a hydrocarbon and an oxygen-containing gas in the presence of a suitable catalyst, more particularly to an improved process for the manufacture of a nitrile, such as acrylonitrile, together with hydrogen cyanide. The present invention is directed to the process for quenching the hot gaseous product stream and removing ammonia (NH3) in the reaction effluent. This quenching stops unwanted side reactions that result in polymerized acrylonitrile, acrolein aldehyde, and other undesirable high molecular weight hydrocarbons. This quenching removes particulates and some contaminants from the hot gaseous product stream.

BACKGROUND OF THE INVENTION

Many petrochemical products are produced by the oxidation of an appropriate hydrocarbon in the vapor phase over a suitable catalyst. For example, unsaturated nitrites are produced by the ammoxidation of a saturated or olefinically unsaturated hydrocarbon with oxygen in the presence of ammonia and an appropriate catalyst. Similarly, alkylene oxides are produced by the oxidation of lower alkanes or alkenes with oxygen in the presence of an appropriate catalyst. The invention is particularly aimed toward the production of acrylonitriles. However, its utility in any process utilizing air or oxygen as a reactant will be appreciated by one skilled in the art.

A popular method for producing nitrites is the so-called ammoxidation method in which an alkene, such as propylene or isobutene, or an alkane is catalytically reacted with ammonia and oxygen at a high temperature in a gas phase in the presence of the catalyst. Air is generally used as the source of the oxygen because of its low cost and ready availability. Ammonia is supplied in excess to maximize nitrites.

The synthesis reaction can be carried out in any suitable reactor, such as a fixed, fluidized or transport bed reactor. The reactions generally take place at very high temperatures. The reactor effluent is a hot gas that comprises the petrochemical product, and generally unwanted byproducts, carbon monoxide, carbon dioxide, water, air, unreacted hydrocarbons, and ammonia. The reaction equipment train generally consists of a reactor, a petrochemical recovery unit such as a scrubber, in which the product is recovered from the reactor effluent gases by means of water or other solvent, means of further purifying the product, and means for further treating the scrubbed effluent gases.

A major problem associated with the gas phase production of a petrochemical by the oxidation of hydrocarbons is that since the reaction is carried out at elevated temperatures, the products and un-converted feedstock continue to react after the product effluent stream exits the reactor. The product polymerizes, reacts with other constituents in the gas stream, and forms other undesirable high molecular weight hydrocarbons. These many and varied side reactions consume product and create waste which must be separated and disposed of. This waste includes nitrile polymers, acrylic acid polymers, polymerized acrylonitrile, acrolein aldehyde, and numerous other undesirable high molecular weight hydrocarbons. Some undesirable reactions are favored at high pH. Due to high pH condensate caused by excess ammonia, effluent below the dew point temperature is particularly vulnerable. The reactions are very fast, and it is desirable to stop these reactions as quickly as possible and prevent high pH reactions which give yield losses. Much of these contaminants are removed in the gas quench operation. The key elements for a successful quench are to reduce the temperature of the gaseous effluent and to remove ammonia. The undesired side reactions stop once the gas has been quenched. Quenching in the subsequent discussion refers to both temperature reduction and to ammonia removal.

A second problem associated with the gas phase production of a petrochemical by the oxidation of hydrocarbons is that since the reaction is carried out at elevated temperatures, there is an ever-present danger of a fire or an explosion in the reactor, or in the equipment or pipelines associated with the reactor. Accordingly, efforts are constantly made to maintain conditions in the reactor and associated equipment such that the mixture remains outside of the flammability range, or at least out of the autoignition range.

The flammability and autoignitability of a gaseous hydrocarbon-oxygen mixture is dependent upon the composition, the pressure, and the temperature of the gaseous mixture. At low temperatures, the gaseous mixture may have a relatively small flammability range, but as the temperature of the mixture rises, its flammability range increases. Also, as the water vapor content rises due to quenching, the flammability falls due to dilution. As the temperature rises, a point is eventually reached at which the mixture becomes autoignitable. When this point is reached, the mixture may ignite and explode, which event can result in damage to equipment and serious injury or death to persons in the vicinity.

U.S. Pat. No. 3,885,928 describes a process for recovery of the hydrocarbon product produced by the ammoxidation process. This process utilized a quench column to cool the reactor effluent. The patent described a quench column as a device for contacting the hot gas with a counterflowing aqueous stream, though it also stated that an aqueous spray contacts the hot effluent gases. A problem with a quench column is that the quenching process takes a long time, relative to the side reactions that are occurring. Quench columns generally take between about 250 milliseconds and about 700 milliseconds or more to cool the gas. This relatively slow quench is in part because the power input to generate the vapor-liquid contact is relatively low.

U.S. Pat. No. 3,936,360 describes a process where gas cooling is accomplished by first cooling the gas with a heat exchanger, and then injecting the quench liquid into the flowing gas in the same direction as the flowing gas, followed by passing the gaseous stream containing acrylonitrile or methacrylonitrile resulting from the quench to an absorber where water and the gases are contacted in concurrent flow to remove substantially all the acrylonitrile or methacrylonitrile. The aqueous stream containing substantially all the acrylonitrile or methacrylonitrile is then passed through a series of distillation columns and separators for separation and purification of product acrylonitrile and derivatives thereof, and quench fluid is obtained from the bottoms of the final product distillation process. The quench process begins in the pipeline leading to the quench column (called a gas washer), wherein water is sprayed into the gas. The gas washer used a spray nozzle near the top of the quench column to introduce water droplets which contact the gaseous stream. The patent calls this a jet washing device in which a large amount of water is circulated and sprayed onto the reactor effluent. The patent clearly shows the spray to be concurrent with the direction of gas flow. If the washing water is not cooled, the water partially flashes in the gas washer.

Other patents describe processes wherein the quench water is obtained from subsequent separation and product purification steps. For instance, U.S. Pat. No. 4,166,008 describes a process that obtains quench water from the bottoms of a second product recovery distillation tower. U.S. Pat. No. 3,936,360 describes a process that obtains quench water from the bottoms of a hydrogen cyanide recovery distillation tower. Hydrogen cyanide is often produced with acrylonitriles.

SUMMARY OF THE INVENTION

The present invention provides an improvement in a process and apparatus for manufacturing petrochemicals by the vapor phase oxidation of a hydrocarbon with oxygen in the presence of a suitable catalyst. The invention comprises contacting the gaseous product stream with a quench fluid in a reverse jet scrubber, preferably with upflow of liquid and downflow of gas. A key element of the success for this arrangement is is the greater atomization of liquid that is obtained due to the greater power input available for atomization of the quench liquid. The power input is adjusted by raising the velocity of the gas and liquid. The quench fluid is injected counter current to the gas flow. The quench fluid impacts the gas stream which is flowing at sufficient velocity to reverse the direction of flow of quench fluid. This creates a zone of intense mixing where the gas is quenched very quickly, i.e., in 100 milliseconds or less. This quick quench stops undesired side reactions, in part by removing reactants such as ammonia and in part by cooling the gas. The quench fluid also removes impurities, including heavy polymers and catalyst fines. The quench fluid introduction means is located downstream of the reaction zone, and is preferably located near the outlet of the ammoxidation reactor.

In some applications of the present invention, the liquid flow can be downflow and the gas can be upflow, and in others the flows can be in the horizontal plane or even at an angle to the vertical plane. As long as the flows are opposed and the gas velocity is sufficiently high, the gas will capture the liquid and reverse the flow direction of the liquid and in the process of reversal generate the turbulence needed for atomization. However, in the acrylonitrile/hydrogen cyanide application the preferred embodiment is with upflow of liquid and downflow of vapor. This is because the need to minimize the opportunity for regions of stagnant liquid and poor contact, which can result in corrosion, polymer growth, and bypass.

In one embodiment of the invention the gas quench fluid is provided from an external source. In an alternate embodiment, expended quench fluid is condensed and separated from the petrochemical-depleted gas stream and used as the quench stream. In a third embodiment, the quench fluid is obtained from a process stream emanating from a subsequent recovery or purification step. An essential element for the acrylonitrile/hydrogen cyanide application of the invention is that the quench fluid contains acid to facilitate removal of ammonia from the gas stream.

In a preferred embodiment, the quench fluid that is not vaporized is recirculated. In a more preferred embodiment, impurities and contaminants are removed from the quench fluid prior to recycle. In a most preferred embodiment, the quench fluid is not cooled during recirculation, and the cooling process is essentially adiabatic, with the sensible heat of the hot gaseous stream being converted to latent heat in the form of vapor. Increased recycle of liquid increases the intensity of the quenching operation and reduces the time required. However, the increased recycle comes at the expense of additional pump, and hence the amount of recycle is one of the key variables in the invention.

DETAILED DESCRIPTION OF THE INVENTION

Figure 1:
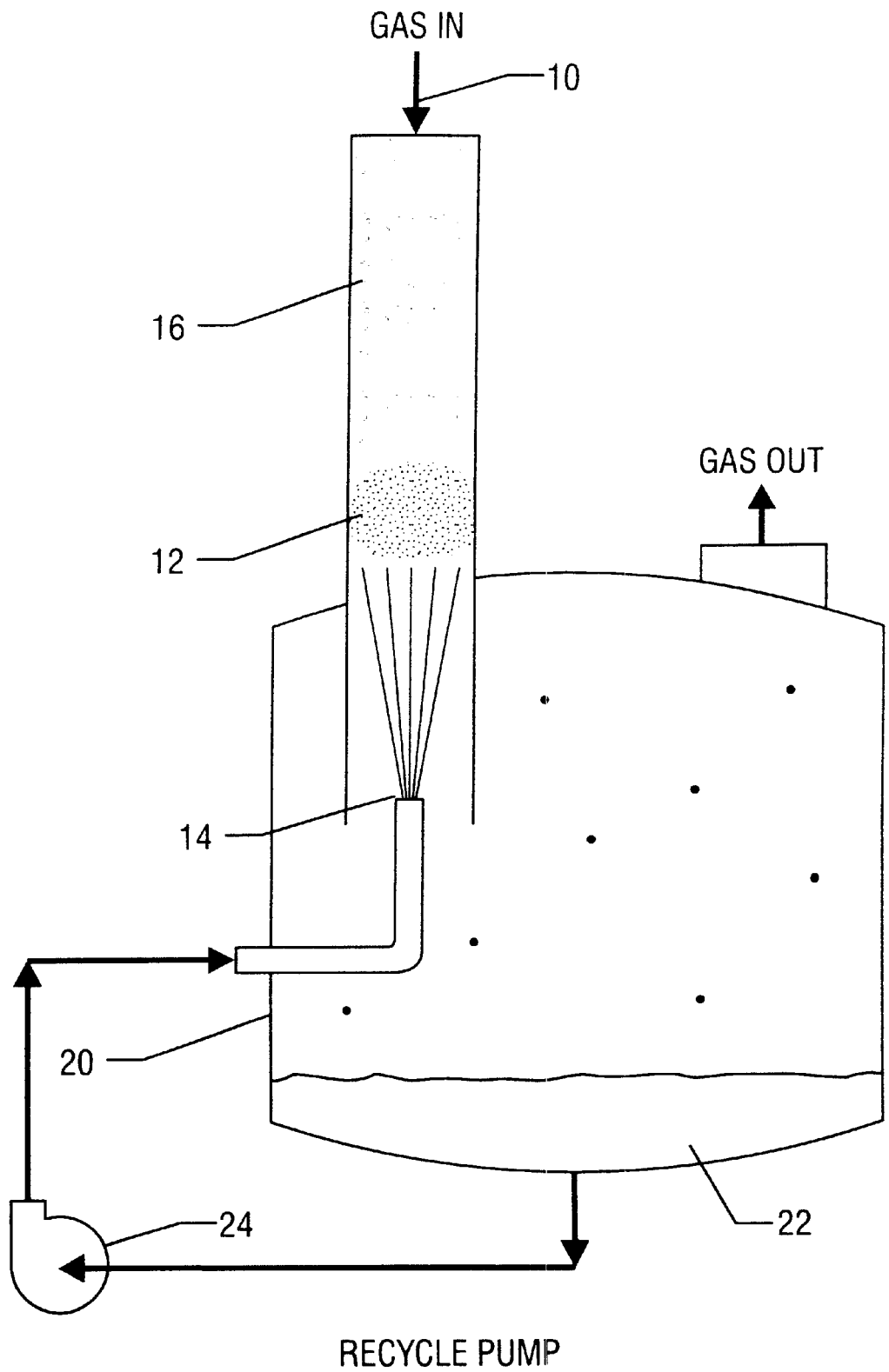
FIG. 1 is a drawing of a reverse jet scrubber with a recycle pump which is a typical embodiment of this invention.

The process of the invention can be used for the manufacture of any petrochemical that is produced by the gas phase reaction at elevated temperatures of a hydrocarbon with oxygen. Typical petrochemical manufacturing processes in which the invention can be employed are the manufacture of an olefinically unsaturated nitriles by the reaction of lower alkanes or alkenes with oxygen and ammonia. In a preferred embodiment of the present invention, the process is performed with the reactor effluent obtained from the ammoxidation of propylene, ammonia and oxygen to produce acrylonitrile. The reaction is carried out at a temperature of between the ranges of about 260° to 600° C., but the preferred temperature range is 310° to 500° C., 350° to 480° C. being especially preferred. As or shortly after the hot gaseous product stream leaves the ammoxidation reaction zone, a quench fluid is injected into the stream to rapidly cool it to below the autoignition temperatures of its flammable components.

The subject of this invention is the passing of the hot gaseous product stream (item 10 in FIG. 1) through a reverse jet scrubber where the gas is quenched by contact with a reverse jet of fluid. Such reverse jet scrubbers are described in U.S. Pat. No. 3,803,805, which is expressly incorporated herein by reference, and are commercially available from Monsanto Enviro-Chem Systems, Inc., St. Louis, under the trademark DYNAWAVE (Registered TM). The gas flows through a conduit (item 16 in FIG. 1) into which a jet of quenching fluid is injected. The gas flow rate is maintained at a velocity of at least the flooding velocity of about 1500 feet per minute, which is the criterion for reversing the flow direction of the injected liquid. It is recognized by those skilled in the art that the actual velocity required will vary with the gas and liquid physical properties such as phase densities. The term flooding velocity is meant the velocity where the gas stream is sufficient to hold up the liquid in the conduit. This velocity is typically between 1000 feet per minute and 2000 feet per minute, but its actual value depends on many factors. Because the undesired side reactions in the hot gaseous effluent, very quick quenching is desired. The preferred superficial gas velocity through the reverse jet gas scrubber is greater than about 1500 feet per minute, preferably between about 3000 feet per minute to about 6000 feet per minute, and most preferably between about 4000 feet per minute and about 5000 feet per minute. All gas velocities are superficial gas velocities, which are determined by dividing the volumetric flow rate by the cross-sectional area of the reverse jet scrubber at or near the point where the injected water forms a "standing wave " or a "froth zone" which is where the bulk of water changes direction of flow. See item 12 in FIG. 1, illustrating the froth zone. The bulk of the quenching takes place in this froth zone and in subsequent concurrent gas and droplet flow. The conduit may be partially constricted to increase the superficial gas velocity at the froth zone.

The quenching fluid is injected through an orifice (item 14 in FIG. 1) at sufficient velocity to provide at least about one jet horsepower per square foot of cross-sectional area of the conduit. Two or more jet horsepower per cross sectional square foot of the conduit is preferred, and three or more horsepower per cross sectional square foot of conduit is more preferred. The quenching fluid is injected counter-currently to the gas.

In a preferred embodiment of the invention, quench fluid is injected through one or more nozzles designed to inject fluid as droplets or a disperse spray, and designed so that the droplets or spray fill reach the entire cross-sectional area where gas flows. This will reduce the power, in the form of gas and injected fluid velocities, needed to obtain the turbulence necessary for quick quenching. Such nozzles will also help eliminate bypass, where a small flowpath may exist that extends substantially through the reverse jet scrubber wherein the quench fluid and gas are not brought into intimate contact. The preferred nozzles often have a high pressure drop to develop the small droplet size and to inject these droplets with sufficient velocity into the gas stream. In addition, the nozzles are preferably placed and designed such that the froth front wherein the direction of flow of the quench fluid reverses is stationary.

The quench fluid impacts the gas stream which is flowing at sufficient velocity to reverse the direction of flow of quench fluid. This creates a zone of intense mixing where the gas is quenched very quickly, i.e., in 100 milliseconds or less. Most of the ammonia, greater than 95%, is removed from the gaseous stream at the same time. A preferred embodiment removes greater than 98% more preferred 99% of the ammonia. This quick quench and the removal of ammonia stops undesired side reactions.

This reverse jet scrubber provides efficient, very quick gas scrubbing with relatively low pressure drops. The quickness of the quench is particularly important, however, low pressure drop is also essential to plant operation. The gas stream from a reactor generally has a high flow rate, and the pressure in the reactor is often close to one atmosphere gauge pressure. The reverse jet scrubber provides a pressure drop of less than about 1 psi, which is low considering the very quick quench.

Typical effluent flow out the reactor is at a temperature of about 455° C. and at a pressure that is about 1 atmosphere. This gas is often cooled somewhat in a heat exchanger where latent heat of the gas generates steam for use in the plant or for export. However, it is not desirable to cool the gas below about 240° C., because of the tendency to condense liquid on the walls of the heat exchanger as the gas is cooled to lower temperatures. In addition, undesirable high molecular weight hydrocarbons deposit onto the heat exchangers and impair exchanger efficiency, as the desired gas exit temperature decreases. Cooling the gaseous effluent below about 240° C. is best done by a quenching process.

In a preferred embodiment called a hot quench, the quench fluid is water that is circulated without extensive external cooling, and the gas temperature will drop to between about 75° C. and about 90° C. as the gas passes through the reverse jet scrubber. Cooling is essentially adiabatic, with the sensible heat in the hot gaseous product being converted to latent heat in water vapor. Therefore, regardless of whether the quench fluid is recycled or not, there must be a ready supply of quench fluid to make up losses due to vaporization.

In another preferred embodiment, the gas effluent is cooled via a heat exchanger from about 455° C. to about 240° C., and then the gas is quenched with water in a reverse jet scrubber. The gas temperature in such a system will drop to between about 75° C. and about 90° C. as the gas passes through the reverse jet scrubber.

Another novel aspect of the invention is the system in which the process of the invention is carried out. According to one embodiment, the system comprises a hydrocarbon reactor, an optional heat exchanger, a reverse jet quenching system, a petrochemical product recovery unit, such as a scrubber or a condenser, and product separation and purification systems. The process of the present invention comprises transporting the reactor effluent obtained during the ammoxidation of propylene or isobutylene to a reverse jet scrubber wherein the hot effluent gases are cooled by contact with an aqueous spray, passing the cooled reactor effluent overhead to an absorber column wherein the crude acrylonitrile or methacrylonitrile is absorbed in water, and then passing the aqueous solution containing the acrylonitrile or methacrylonitrile to a product recovery system comprising at least one separator, or at least one distillation column, or both. The quench fluid may be obtained from the aqueous waste streams from these decanters or distillation columns. This is a preferred embodiment because it utilizes waste streams from the subsequent processing steps that contain minor quantities, i.e., less than 1% by weight, of product. This removes the need to dispose of this waste stream and will result in increased recovery of product.

The quench fluid is introduced downstream of the reaction zone, preferably near the outlet of the oxidation reactor, or the optional heat exchanger by means of a reverse jet scrubber. The quench fluid will remove ammonia and entrap contaminants such as polymerized product and particulates. These contaminants are removed from the quench fluid and disposed of.

The quench fluid can be any liquid that will not interfere with the recovery of the desired product, that vaporizes at a temperature near the temperature it is desired to cool the effluent stream to, and preferably which is not flammable or explosive under the conditions existing in the reaction system of the invention. Typical quench fluids in the process of the invention are water, an aqueous mixture comprising a acid to neutralize and remove ammonia, or an aqueous mixture having as its source a unit used for product separation and recovery and therefore comprising minor quantities of product or contaminants. From a practical standpoint the preferred quench fluid is an aqueous waste stream from a subsequent purification process, since this fluid are inexpensive and readily available.

The preferred quenching fluid should contain an acid such that essentially all, i.e., more than 95%, of the ammonia in the gas can be stripped from the gas. It is preferred that the quenching fluids have sufficient acid to neutralize all absorbed ammonia and still maintain the fluid pH below about 5.

The quench fluid may be cooled to any desired temperature. However, a preferred embodiment does not employ cooling, but rather circulates hot quench fluid mixed with some make-up fluid that contains residual quantities of product. Gas cooled to below 90° C. no longer sustains unwanted side reactions. The principal cooling mechanism is the conversion of sensible heat in the gaseous product stream to latent heat in the form of a condensable vapor.

The quantity of quenching fluid injected should be at least sufficient to lower the temperature of the gaseous effluent product to the desired level. If the minimum quantity of quenching fluid is injected, such that essentially all of the injected quench fluid is vaporized, then undesirable deposition of contaminants and particles will result, and ammonia will not be removed. The invention therefore calls for more than the minimum quantity of quenching fluid to be injected. The quantity of quench fluid injected in the reverse gas scrubber should be between about 20 times the quantity of fluid that will be vaporized to about 300 times the quantity of fluid that will be vaporized, and preferably between about 80 times the quantity of fluid that will be vaporized to about 180 times the quantity of fluid that will be vaporized, and most preferably between about 100 times the quantity of fluid that will be vaporized to about 140 times the quantity of fluid that will be vaporized. This liquid is later separated from the gas by conventional means, such as a separator depicted as item 20 FIG. 1. Of course, those skilled in the art would recognize that the quantity of fluid vaporized will depend principally on the temperature is and pressure of the effluent gas stream.

The addition of excess water into the gaseous stream may result in a large waste stream that must be treated or disposed of and will result in ever increasing loss of product due to solubilization of product in the quenching fluid. Lost product and waste streams will both be minimized if the quench fluid is recycled, and at least a portion of the quench fluid should be recycled. A recycle pump is included as item 24 in FIG. 1. Of course, to prevent fouling the entrained particulates and contaminants will need to be removed. These materials can be separated from the recovered quench fluid or, alternatively, a portion of the recovered quench fluid can be treated as a waste stream.

In another embodiment of the present invention there are two reverse jet scrubbers in series that treat the hot effluent product gas. The first reverse jet scrubber is used primarily for quenching purposes and to remove contaminants. The second reverse jet scrubber can be used to further cool the effluent gas stream and also to recover reactants or product by dissolution in the injected fluid. In this second reverse jet scrubber, cooling of the injected quench fluid is necessary. The second quench fluid may have more rigorous control of pH, via addition of acid, to make sure the ammonia is removed from the gas stream. Most of the quench fluid that vaporized in the first reverse jet scrubber will condense in the second reverse jet scrubber.

The pressure under which the reverse jet scrubber operates is not important. However, since most heat loss by the effluent gas is caused by the vaporization of water, and because the effluent gas stream leaving the reverse jet scrubber can only be saturated with that fluid at a given temperature and pressure, lower pressures will generally result in lower resultant temperatures. The pressure is often maintained at about 1 to 15 psig and preferably between 3 to 7 psig.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for the manufacture of a nitrile product comprising producing a nitrile compound in a reactor by ammoxidation of a feed comprising a hydrocarbon, water vapor, ammonia, and oxygen, thereby producing a hot gaseous effluent comprising a nitrile compound and unreacted reactants and reaction products, and transporting the hot gaseous effluent through a reverse jet scrubber wherein the hot gaseous effluent is cooled by contact with an acidic quenching fluid injected counter-currently to the direction of the gaseous effluent flow, wherein ammonia is removed while maintaining a pH below about 5 throughout the quenching fluid, wherein the gaseous effluent is transported through the reverse jet scrubber at sufficient superficial velocity to reverse the flow direction of the injected quenching fluid, and wherein a portion of the injected quenching fluid is vaporized.

2. The process of claim 1 where the feed further comprises inerts.

3. The process of claim 1 wherein the quenching fluid is further recovered from the gaseous effluent downstream of the reverse jet scrubber, and wherein said recovered quenching fluid is recirculated by injecting said recovered quenching fluid counter-currently to the direction of the gas flow in the reverse jet scrubber.

4. The process of claim 1 wherein the quenching fluid comprises a largely aqueous stream and an acid present in sufficient quantity to neutralize all ammonia in the gas and maintain a pH below 5 throughout the quenching operation.

5. The process of claim 3 wherein the quenching fluid comprises water, sulfuric acid, recovered quenching fluid or combinations thereof.

6. The process of claim 2 wherein the recovered quenching fluid is not actively cooled prior to recirculating the fluid through the reverse jet scrubber.

7. The process of claim 3 wherein the quenching fluid comprises water, sulfric acid, recovered quenching fluid, or combinations thereof, and wherein contaminants are removed from the recovered quenching fluid prior to recirculating the recovered quenching fluid through the reverse jet scrubber.

8. The process of claim 1 wherein the superficial gas velocity in the reverse jet scrubber is between about 1500 feet per minute and about 7000 feet per minute.

9. The process of claim 1 wherein the superficial gas velocity in the reverse jet scrubber is between about 2500 feet per minute to about 6000 feet per minute.

10. The process of claim 1 wherein the superficial gas velocity in the reverse jet scrubber is between about 4000 feet per minute and about 5000 feet per minute.

11. The process of claim 1 wherein the quantity of quenching fluid injected in the reverse gas scrubber is between about 20 times the quantity of fluid that is vaporized and about 300 times the quantity of fluid that is vaporized.

12. The process of claim 1 wherein the quantity of quenching fluid injected in the reverse gas scrubber is between about 80 times the quantity of fluid that is vaporized and about 180 times the quantity of fluid that is vaporized.

13. The process of claim 1 wherein the quantity of fluid injected in the reverse gas scrubber is between about 100 times the quantity of fluid that is vaporized and about 140 times the quantity of fluid that is vaporized.

14. The process of claim 2 wherein the quantity of quenching fluid injected in the reverse gas scrubber is between about 20 times the quantity of the quenching fluid that is vaporized and about 300 times the quantity of the quenching fluid that is vaporized.

15. The process of claim 2 wherein the quantity of quenching fluid injected in the reverse gas scrubber is between about 80 times the quantity of quenching fluid that is vaporized and about 180 times the quantity of quenching fluid that is vaporized.

16. The process of claim 2 wherein the quantity of quenching fluid injected in the reverse gas scrubber is between about 100 times the quantity of quenching fluid that is vaporized and about 140 times the quantity of quenching fluid that is vaporized.

17. The process of claim 1 wherein a heat exchanger located between the reactor and the reverse jet scrubber cools the hot gaseous effluent prior to the gas passing through the reverse jet scrubber.

18. The process of claim 1 wherein the quenching fluid is injected into the reverse jet scrubber through one or more orifices.

19. The process of claim 1 wherein the quenching fluid velocity at the orifice is sufficient to provide at least 1 jet horsepower per square foot of cross-sectional area of the reverse jet scrubber.

20. The process of claim 1 wherein the reverse jet is oriented with downward flow of gas and upward flow of liquid and wherein the liquid is injected so as to provide a uniform distribution into the gas.

21. The process of claim 1 wherein the quenching fluid velocity at the orifice is sufficient to provide at least 3 jet horsepower per square foot of cross-sectional area of the reverse jet scrubber.

22. The process of claim 1 wherein the hot gaseous effluent entering the reverse jet scrubber is cooled to a temperature below about 120° C. in less than about 100 milliseconds after entering the froth zone.

23. The process of claim 1 wherein the hot gaseous effluent entering the reverse jet scrubber is cooled to a temperature below about 100° C. in less than about 100 milliseconds after entering the froth zone.

24. Process of claim 1 wherein the ammonia removal is greater than 95%.

25. Process of claim 1 wherein the ammonia removal is greater than 98%.

26. Process of claim 1 wherein the ammonia removal is greater than 99%.

27. A process for the manufacture of a nitrile compound comprising producing a nitrile compound in a reactor by ammoxidation of a feed comprising a hydrocarbon, water vapor, ammonia, and oxygen, thereby producing a hot gaseous effluent comprising a nitrile compound and unreacted reactants and reaction products, and transporting the hot gaseous effluent through a reverse jet scrubber wherein the hot gaseous effluent is cooled by contact with an acidic quenching fluid injected counter-currently to the direction of the gaseous effluent flow, wherein ammonia is removed while maintaining a pH below 5 in the quenching fluid throughout the quenching operation, wherein the gaseous effluent is transported through the reverse jet scrubber at sufficient superficial velocity to reverse the flow direction of the injected quenching fluid, and wherein a portion of the injected quenching is vaporized.

* * * * *